United States Patent
Schmitz et al.

(10) Patent No.: US 10,092,673 B2
(45) Date of Patent: *Oct. 9, 2018

(54) HYDROGEL FIBERS AND FIBROUS STRUCTURES

(75) Inventors: Wiebke Schmitz, Mannheim (DE); Julia Schmidt, Essen (DE); Bernd Schlesselmann, Weinheim (DE); Gunter Scharfenberger, Frankenthal (DE)

(73) Assignee: Carl Freudenberg KG, Weinheim (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/878,236

(22) PCT Filed: Jul. 29, 2011

(86) PCT No.: PCT/EP2011/003808
§ 371 (c)(1),
(2), (4) Date: Apr. 8, 2013

(87) PCT Pub. No.: WO2012/048768
PCT Pub. Date: Apr. 19, 2012

(65) Prior Publication Data
US 2013/0323195 A1  Dec. 5, 2013

(30) Foreign Application Priority Data
Oct. 15, 2010 (DE) .................. 10 2010 048 407

(51) Int. Cl.
*A61L 15/22* (2006.01)
*D01D 10/02* (2006.01)
*A61L 26/00* (2006.01)
*A61L 27/56* (2006.01)
*A61L 17/10* (2006.01)
*A61L 27/16* (2006.01)
*A61L 15/42* (2006.01)
*A61L 15/24* (2006.01)
*A61L 27/52* (2006.01)
*D01F 6/50* (2006.01)
*D01F 6/14* (2006.01)
*D01F 8/10* (2006.01)
*D01F 6/34* (2006.01)

(52) U.S. Cl.
CPC ............ *A61L 15/225* (2013.01); *A61L 15/24* (2013.01); *A61L 15/425* (2013.01); *A61L 17/10* (2013.01); *A61L 26/0014* (2013.01); *A61L 26/0085* (2013.01); *A61L 27/16* (2013.01); *A61L 27/52* (2013.01); *A61L 27/56* (2013.01); *D01D 10/02* (2013.01); *D01F 6/14* (2013.01); *D01F 6/34* (2013.01); *D01F 6/50* (2013.01); *D01F 8/10* (2013.01)

(58) Field of Classification Search
None
See application file for complete search history.

(56) References Cited

U.S. PATENT DOCUMENTS

| 4,187,342 | A | * | 2/1980 | Holst ..................... D04H 1/425 156/246 |
| 4,440,711 | A | * | 4/1984 | Kwon et al. .................. 264/185 |
| 4,552,138 | A | * | 11/1985 | Hofeditz ............. A61L 26/0014 424/445 |
| 5,725,601 | A | * | 3/1998 | Tajiri ..................... A61L 15/28 162/100 |
| 5,985,443 | A | | 11/1999 | Honeycutt |
| 6,176,973 | B1 | * | 1/2001 | Norlander ............... A61L 15/28 162/157.6 |
| 2004/0105880 | A1 | | 6/2004 | Turner |
| 2008/0311815 | A1 | * | 12/2008 | Gupta et al. .................. 442/351 |
| 2013/0101805 | A1 | * | 4/2013 | Altshuler et al. ............. 428/172 |

FOREIGN PATENT DOCUMENTS

| DE | 44610 | 11/1966 |
| EP | 0745708 A2 | 12/1996 |
| WO | WO 0130407 A1 | 5/2001 |
| WO | WO 2005/103097 A1 | 11/2005 |
| WO | WO 2009/085679 A1 | 7/2009 |

OTHER PUBLICATIONS

Jin, Xing, and You-Lo Hsieh. "pH-responsive swelling behavior of poly (vinyl alcohol)/poly (acrylic acid) bi-component fibrous hydrogel membranes." Polymer 46.14 (2005): 5149-5160.*
Bolto, Brian, et al. "Crosslinked poly (vinyl alcohol) membranes." Progress in Polymer Science 34.9 (2009): 969-981.*
Kenneth Kar Ho Wong et al: "Effect of Annealing on Aqueous Stability and Elastic Modulus of Electrospun Poly (Vinyl Alcohol) Fibers", Journal of Materials Science, Kluwer Academic Publishers, BO, vol. 45, No. 9, Jan. 26, 2010, pp. 2456-2465, XP019790792, ISSN: 1573-4803, p. 2456-p. 2458, Tables 1,3.
Suzuki A et al: "Mechanical Properties and Superstructure of Poly (Vinyl Alcohol) Fibers Annealed Under Extremely High Tension", Kobunshi Ronbunshu (Japanese Polymer Science and Technology), Society of Polymer Science, Tokyo, JP, vol. 51, No. 3, Jan. 1, 1994, pp. 201-207, XP000445867, ISSN: 0386-2186, Englische Zusammenfassung; p. 207.

(Continued)

Primary Examiner — John Pak
Assistant Examiner — Daniel L Branson
(74) Attorney, Agent, or Firm — Leydig, Voit & Mayer, Ltd.

(57) ABSTRACT

A plurality of fibers or one-dimensional, two-dimensional, or three-dimensional fibrous structures are provided, having fibers from a first raw fiber material. The first raw fiber material contains unsubstituted or partially substituted polyvinyl alcohol and/or unsubstituted or partially substituted polyvinyl alcohol copolymer. The fibers can be crosslinked by tempering the fibers or fibrous structures, with the result that the fibers or the fibrous structure are configured to be gel, in particular hydrogel, fibers or fibrous structures and have excellent stability.

14 Claims, No Drawings

(56) References Cited

OTHER PUBLICATIONS

Liqian Huang et al: "Effects of Heat Treatment on Tensile Properties of High-Strength Poly (vinyl alcohol) Fibers." Journal of Applied Polymer Science, vol. 78, p. 237-p. 242, John Wiley & Sons, Inc., Dec. 2000.

Marcel Dekker, Inc. "Library of Congress Cataloging in Publication Data," ISBN 0-8247-7434-5, Sep. 3, 1986.

* cited by examiner

HYDROGEL FIBERS AND FIBROUS STRUCTURES

CROSS-REFERENCE TO RELATED APPLICATIONS

This application is a U.S. National Phase application under 35 U.S.C. § 371 of International Application No. PCT/EP2011/003808, filed on Jul. 29, 2011, and claims benefit to German Patent Application No. DE 10 2010 048 407.5, filed on Oct. 15, 2010. The International Application was published in German on Apr. 19, 2012, as WO 2012/048768 A1 under PCT Article 21(2).

FIELD

The present invention relates to fibers or one-dimensional, two-dimensional or three-dimensional fibrous structures, and to an associated method of production. Furthermore the invention relates to the use of such fibers or fibrous structures as carrier materials, hygiene products, cosmetic products or the like and bandages or wound dressings, containing such fibers or fibrous structures.

BACKGROUND

From WO 01/30407 A1 a method for the production of hydrogels for use as wound dressings is known, by which burns or other skin injuries can be treated. In the course of the method an aqueous solution of polyvinyl alcohol, agar-agar and at least one further natural polymer is prepared. This solution is introduced at 70-80° C. into one-way plastic containers and sealed. After cooling to room temperature the samples introduced into the one-way plastic containers are irradiated and thus sterilised.

In WO 2005/103097 A1 hydrogels are described which include at least one polyvinyl alcohol star polymer. In this case the hydrogels are produced by repeated freezing and thawing of an aqueous solution containing at least one polyvinyl alcohol star polymer and optionally further components. Furthermore such hydrogels can be produced by the action of ionising radiation on an aqueous solution containing at least one polyvinyl alcohol star polymer or by a reaction of a polyvinyl alcohol star polymer in aqueous solution with cross-linking reagents.

A disadvantage of the currently known methods for production of hydrogels, in particular for wound treatment, is the costly mode of production and the problematic further processing of the hydrogels, and also the possible occurrence of chemical contaminants in the hydrogels which are cross-linked for example by a chemical reaction. Moreover hydrogel films, in contrast to fibers and fibrous structures, have a smaller surface, so that they have a lesser absorption capacity for water or aqueous solutions. Particularly when polyvinyl alcohol is used as raw material for hydrogels care should be taken to ensure that the polyvinyl alcohol has a correspondingly high degree of cross-linking, since otherwise no hydrogels but solutions of the polyvinyl alcohol in the corresponding liquid medium are formed. Consequently a high stability of the polyvinyl alcohol relative to the solubility in water or in aqueous solutions is desirable. Moreover polyvinyl alcohol and polyvinyl alcohol copolymers are distinguished by a high biocompatibility so that there is an increasing need for further embodiments of hydrogels or hydrogelling materials with polyvinyl alcohol and/or polyvinyl alcohol copolymers which are also cost-effective and simple to produce and enable problem-free further processing.

SUMMARY

An aspect of the invention provides a plurality of fibers, comprising: first fibers made of a first raw fiber material comprising an unsubstituted polyvinyl alcohol, a partially substituted polyvinyl alcohol, an unsubstituted polyvinyl alcohol copolymer, a partially substituted polyvinyl alcohol copolymer, or a mixture thereof, wherein the plurality is configured to be gelling, and wherein the plurality is cross-linked by tempering.

DETAILED DESCRIPTION

An object of the present invention therefore relates to the object of providing an improved embodiment or at least an alternative embodiment for fiber or fibrous structures, use thereof, and an associated production method, and for bandages or wound dressings, which embodiments are in particular distinguished by simplified, cost-effective production and enable problem-free further processing and/or application.

An object of the invention is achieved according to the invention by the subject matters of the independent claims. Advantageous embodiments are the subject matter of the dependent claims.

Surprisingly it could now be ascertained that fibers or fibrous structures which contain polyvinyl alcohol or polyvinyl alcohol copolymers can be treated by tempering so that they have gelling, in particular hydrogelling, characteristics after the tempering and also have a high stability at least relative to the solubility in water or aqueous solutions. Moreover the fibers or fibrous structures are distinguished by a particularly high absorption of water or aqueous solutions, in particular 0.9% aqueous sodium chloride solution (physiological saline solution).

Thus in a first feature of the invention fibers or fibrous structures are proposed, one-dimensional, two-dimensional, three-dimensional, comprising fibers from a first raw fiber material which contains unsubstituted or partially substituted polyvinyl alcohol and/or unsubstituted or partially substituted polyvinyl alcohol copolymers, wherein the fibers are cross-linked by tempering. In this case the fibers or fibrous structures are gelling, in particular hydrogelling.

Advantageously the fibers or fibrous structures can be cross-linked by the tempering, so that on the one hand after the tempering the fibers or fibrous structures have a higher stability at least relative to the solubility in water. On the other hand due to the tempering the fibers or fibrous structures acquire the ability to form a stable gel with water or aqueous solutions, in particular with 0.9% sodium chloride solution. Moreover, contaminants or residues, such as for example spinning aids, brighteners, solvents or the like, can be reduced to an insignificant, hardly detectable concentration by the tempering. Furthermore such fibers or fibrous structures have a high absorption capacity for water, in particular for a 0.9% aqueous sodium chloride solution. Thus toxicologically harmless fibers or fibrous structures, and gels which can be produced therefrom, in particular hydrogels, can be advantageously produced. In this case the percentage information for the sodium chloride solution is given in % by weight.

Consequently the object referred to in the introduction is achieved.

A fiber is understood to be a flexible structure which is thin in relation to its length. Fibers have a small diameter and can be built up with one another by corresponding bonding processes to produce fibrous structures. Thus a fibrous structure can include a plurality of fibers. A distinction can be made between one-dimensional, two-dimensional and three-dimensional fibrous structures. A one-dimensional fibrous structure has a small width and a small height by comparison with its length. A two-dimensional fibrous structure has a small height by comparison with its length and width. Three-dimensional fibrous structures should be understood to be fibrous structures which have a plurality of layers of two-dimensional fibrous structures. In this case the individual layers of the three-dimensional fibrous structures can be connected to one another by bonding processes described below or in other ways.

Naturally occurring natural fibers may be designated as one-dimensional fibrous structures. Natural fiber yarns can be obtained from washed and processed natural fibers by yarn spinning processes and can constitute one-dimensional fibrous structures. Moreover, from synthetic, natural or modified natural polymers filaments can be produced by means of the dry or wet spinning process and spunlaid nonwovens can be produced by means of the spunlaid process. The filaments may be regarded as one-dimensional fibrous structures, whilst the spunlaid nonwovens can constitute two-dimensional fibrous structures. By cutting and/or curling the filaments staple fibers can be produced which may be classified as one-dimensional fibrous structures. Staple fiber yarns can be produced from staple fibers by yarn twisting. They may be understood as one-dimensional fibrous structures. Yarns made up of filaments can be formed from one filament (monofilament yarn) or from a plurality of filaments (multifilament yarn). They may also be regarded as one-dimensional fibrous structures. Mixed yarns can be produced by yarn spinning of more than one different staple fiber or natural fibre. Yarns such as natural fiber yarns, staple fiber yarns or filament yarns or mixed yarns can be further processed by means of textile engineering processes such as weaving, knitting, warp knitting, embroidery, laying or sewing for example to produce woven, knitted, laid or warp knitted fabrics. The woven, knitted, laid or warp knitted fabrics may be regarded as two-dimensional fibrous structures. By means of nonwoven processes such as carding, the airlaid process or the wetlaid nonwoven process, staple fiber nonwovens or airlaid nonwovens or airlaids, or wetlaid nonwovens can be produced from staple fibers, and may also be regarded as two-dimensional fibrous structures.

Unbonded nonwovens, for example staple fiber or spunlaid nonwovens, can be bonded by bonding processes. Calendering may be used for example as the bonding process. In this process the unbonded nonwovens are guided between rollers, wherein welding surfaces disposed on the rollers create welds in the nonwovens, which welds at least partially penetrate the nonwovens. If spot welds are produced, then the bonding process is designated as a PS (point seal) bonding process. However, the formation of linear welds or welds over the entire surface is possible. Hot air bonding in a through-air dryer can be used as a further bonding process, wherein in this process bonds are produced by fusions at the contact points of the fibers. Furthermore the use of binders or binding agents is likewise conceivable, wherein in this case the fibers are connected to one another via bridges of binder or binding agent. Mechanical bonding processes can also be used, such as for example the needle bonding process in which the bonding is performed by means of needles and/or the water jet bonding process in which water jets are used. Furthermore fulling or felting or the like are also conceivable. A combination of a plurality of bonding processes can also be used. The needle bonding process, the water jet process and/or the PS bonding process are preferably used.

The fibers can be cross-linked by tempering. Thus the fibers themselves and also the fibrous structures which can be produced therefrom can be changed by tempering in such a way that they have a higher stability with regard to the solubility in water, in particular in a 0.9% aqueous sodium chloride solution, and also constitute outstanding gelling agents.

A gel should be understood to be a finely dispersed system consisting of at least one solid and one liquid phase, wherein the solid phase forms a three-dimensional network of which the pores are filled by the liquid phase. Both phases penetrate one another completely and consequently by comparison with a sponge a gel can store the liquid phase in a more stable manner with respect to, for example, pressure. Fibers or fibrous structures according to the invention are designed to be gelling, in particular hydrogelling, and consequently have an outstanding binding capacity for corresponding liquid phases. They are preferably applied in a dry state to the wound and they form stable gels with the wound exudate, thus creating a moist wound climate. Such a moist wound treatment may assist the healing process.

Likewise for moist wound treatment they can be used in gel form with a liquid phase. In this case water is preferably used as liquid phase and particularly preferably a 0.9% aqueous sodium chloride solution, Ringer solution or solutions containing active substance. Consequently gelling should be understood as the ability to form a gel by absorbing a liquid phase, and hydrogelling should be understood as the ability to form a hydrogel, which has as liquid phase water or an aqueous solution, particularly preferably a 0.9%, aqueous sodium chloride solution.

Polyvinyl alcohol is used as the first raw fiber material. At least one polyvinyl alcohol copolymer may also be used. In the case of a polyvinyl alcohol copolymer, polyethylene vinyl alcohol may be used for example.

If polyvinyl alcohol copolymers are used as the first raw fiber material, then further physical and also chemical properties can also be built into the fibers in a targeted manner as appropriate. Thus in the event of use of, for example polyethylene vinyl alcohol, the number of OH groups is reduced. However, other functional groups can also be introduced into the fibers by means of copolymerisation. Thus the polyvinyl alcohol copolymers make further first raw fiber materials available.

Preferably polyethylene vinyl alcohol, polyvinyl alcohol styrene, polyvinyl alcohol vinyl acetate, polyvinyl alcohol vinyl pyrrolidone, polyvinyl alcohol ethylene glycol and/or polyvinyl alcohol, particularly preferably polyethylene vinyl alcohol, polyvinyl alcohol vinyl acetate, polyvinyl alcohol vinyl pyrrolidone, polyvinyl alcohol vinylamine, polyvinyl alcohol acrylate, polyvinyl alcohol acrylamide, polyvinyl alcohol ethylene glycol and/or polyvinyl alcohol and quite particularly preferably polyvinyl alcohol is used as the first raw fiber material. Block copolymers and/or graft copolymers and/or block and graft copolymers, statistical or alternating systems and any mixtures of these can also be used as first raw fiber material.

Both the polyvinyl alcohol copolymer and the polyvinyl alcohol may be used in unsubstituted or partially substituted form. In the event of the partial substitution the substitution of the OH groups by —(C═)—R or —OR is conceivable, wherein R in each case independently of one another stands for a $C_1$-$C_4$ alkyl group. In this case a $C_1$-$C_4$ alkyl group is understood to be methyl, ethyl, propyl, iso-propyl, 1-butyl, 2-butyl, or tert.-butyl.

In this case the polyvinyl alcohol copolymer or the polyvinyl alcohol can preferably be used at least partially substituted with —O(C═O)—R or —OR or unsubstituted, particularly preferably with —O(C═O)—R, in particular if R stands for ethyl, substituted or unsubstituted and quite particularly preferably unsubstituted.

Furthermore the first raw fiber material may be formed as a polymer blend. In this case a polymer blend is understood to be a physical mixture of at least two polymers from the melt or from the solution.

Advantageously, the resulting polymer blend has different physical properties and possibly also chemical properties by comparison with the polymers used. The properties of the polymer blend are usually a sum of the properties of the polymer blends used. Thus by the use of polymer blends a selection of first raw fiber materials can be further increased.

In this case in order to form such a polymer blend gelling further polymers can be used, such as for example alginates, cellulose ethers, such as carboxymethyl celluloses, methyl celluloses, ethyl celluloses, hydroxymethyl celluloses, hydroxyethyl celluloses, hydroxyalkyl methylcelluloses, hydroxypropyl celluloses, cellulose esters, such as cellulose acetate, oxidised celluloses, bacterial celluloses, cellulose carbonates, gelatines, collagens, starches, hyaluronic acids, pectins, agar, polyacrylates, polyvinyl amines, polyvinyl acetates, polyethylene glycols, polyethylene oxides, polyvinyl pyrrolidones, polyurethanes or non-gelling further polymers, such as for example polyolefins, celluloses, cellulose derivatives, regenerated celluloses such viscoses, polyamides, polyacrylonitriles, polyvinyl chlorides, chitosans, polylactides, polyglycolides, polyester amides, polycaprolactones, polyhexamethylene terephthalates, polyhydroxybutyrates, polyhydroxyvalerates or polyesters.

The blends specified above can be used as homopolymers or copolymers. Block copolymers and/or graft copolymers and/or block and graft copolymers, statistical or alternating systems and any mixtures of these can also be used.

Alginates are understood to be the salts of algic acid, a natural polymer occurring in algae, the two uronic acids α-L-guluronic acid and β-D-mannuronic acid which are 1,4-glycosidically bound. In this case the term "alginate" encompasses E401, E402, E403, E404 and E405 (PGA). The term "polyolefins" encompasses PE, PB, PIB and PP. The term "polyamides" encompasses PA6, PA6.6, PA6/6.6, PA6.10, PA6.12 PA69, PA612, PA11, PA12, PA46, PA1212 and PA6/12. The term "celluloses" encompasses regenerated celluloses such as viscoses, as well as cellulose derivatives and chemically and/or physically modified celluloses. The term "polyesters" encompasses PBT, BC, PET, PEN and UP.

The use of gelling further polymers, unsubstituted or partially substituted polyvinyl alcohol copolymers, such as polyethylene vinyl alcohol, polyvinyl alcohol styrene, polyvinyl alcohol vinyl acetate, polyvinyl alcohol vinyl pyrrolidone, polyvinyl alcohol ethylene glycol, polyvinyl alcohol vinylamine, polyvinyl alcohol acrylate, polyvinyl alcohol acrylamide and/or polyvinyl alcohol is preferred, the use of unsubstituted or partially substituted polyvinyl alcohol copolymers, such as polyethylene vinyl alcohol, polyvinyl alcohol vinyl acetate, polyvinyl alcohol vinyl pyrrolidone, polyvinyl alcohol vinylamine, polyvinyl alcohol acrylate, polyvinyl alcohol acrylamide, polyvinyl alcohol ethylene glycol and/or polyvinyl alcohol is particularly preferred, and the use of unsubstituted polyvinyl alcohol copolymers and/or polyvinyl alcohol for the production of the first raw fiber material formed as polymer blends, containing at least polyvinyl alcohol and/or at least one polyvinyl alcohol copolymer, is quite particularly preferred. Block copolymers and/or graft copolymers and/or block and graft copolymers, statistical or alternating systems and any mixtures of these can also be used.

Moreover the fibers or fibrous structures may additionally include fibers made of at least one second raw fiber material. In this case the at least one second raw fiber materials may be non-gelling or gelling. Thus non-gelling or gelling fibers may be used as further fibers.

A desired behaviour of the fibers or fibrous structures can be improved advantageously by the use of further fibers. Thus it is conceivable by the use of the further fibers to improve the stability of the fibers or fibrous structures by the action of the further fibers as a stabilising structure, in particular in relation to mechanical stress.

Polyolefins, celluloses, cellulose derivatives, regenerated celluloses, such as viscoses, polyamides, polyacrylonitriles, chitosans, elastanes, polyvinyl chlorides, polylactides, polyglycolides, polyester amides, polycaprolactones, polyhexamethylene terephthalates, polyhydroxybutyrates, polyhydroxyvalerates, animal and/or vegetable natural fibers and/or polyesters can be used as non-gelling second raw fiber material; alginates, cellulose ethers, such as carboxymethylcelluloses, methyl celluloses, ethyl celluloses, hydroxymethyl celluloses, hydroxyethyl celluloses, hydroxyalkyl methylcelluloses, hydroxypropyl celluloses, cellulose esters, such as cellulose acetate, oxidised celluloses, bacterial celluloses, cellulose carbonates, gelatines, collagens, starches, hyaluronic acids, pectins, agar, polyvinyl amines, polyvinyl acetates, polyethylene glycols, polyethylene oxides, polyvinylpyrrolidones, polyurethanes and/or polyacrylates can be used as gelling second raw fiber material. The specified second raw fiber materials can be used both as homopolymers and as copolymers. Block copolymers and/or graft copolymers and/or block and graft copolymers, statistical or alternating systems and any mixtures of these can also be used. The simultaneous use of gelling and non-gelling further fibers is also possible. In this case further fibers of a second non-gelling raw fiber material are preferably used. Fibers of polyamide and/or polyester are particularly preferred and fibers of polyester are quite particularly preferred.

The further fibers can also be produced from a second raw fiber material formed as a polymer blend. The advantages already set out above in relation to the first raw fiber material are produced for the further fibers.

Bicomponent fibers and/or multicomponent fibers, gelling or non-gelling, can be used as further fibers. In this case the bicomponent fibers and/or multicomponent fibers with geometric forms such as "core-shell", "side-by-side", "pie or orange type", "matrix with fibrils" can be used. The bicomponent fibers and/or multicomponent fibers can be used for thermal bonding of the nonwovens. When these fibers are heated a thermal bonding of the nonwovens takes place. For example in a core-shell fiber the shell portion melts and thus bonds the nonwoven. Fibers made of polyethylene/polypropylene, polyethylene/polyester, co-polyester/polyethylene terephthalate, polyamide 6/polyamide 6.6, polybutylene terephthalate/polyethylene terephthalate can be used as bicomponent fibers and/or multicomponent fibers.

Advantageously by the use of additional non-gelling fibers the absorption capacity of water, in particular of a 0.9% sodium chloride solution, can be significantly increased by comparison with fibers or fibrous structures without additional non-gelling fibers, since a gel blocking effect which above a predetermined saturation prevents a further absorption of water, in particular of a 0.9% sodium chloride solution, can be reduced by means of the non-gelling fibers. Moreover the fibers or fibrous structures can be mechanically stabilised more strongly by the use of non-gelling fibers and also the shrinkage of the fibers or fibrous structures can be significantly reduced by the addition of non-gelling fibers.

The shrinkage of at least two-dimensional fibrous structures can be determined by stamping out of 10.0 cm×10.0 cm (area 1) large pieces and immersion thereof in a 0.9% aqueous sodium chloride solution. The stamped-out and impregnated pieces are removed from the solution and drained for 2 minutes. Then the size of the pieces is measured (area 2). The shrinkage of the nonwovens can then be calculated according to the following formula:

$$\text{shrinkage } [\%] = 100 - \frac{\text{area 2[cm}^2]}{\text{area 1[cm}^2]} * 100$$

The proportion of further fibers in the fibers or the fibrous structures may amount to 1 to 70% by weight. The proportion is preferably 1 to 65% by weight, particularly preferably 5 to 60% by weight and quite particularly preferably 10 to 50% by weight.

The further fibers can have a fiber titre of 0.9 to 10 dtex. They are preferably used with a fiber titre of 1 to 9 dtex, particularly preferably with a fiber titre of 1.5 to 7 dtex and quite particularly preferably with a fiber titre of 1.9 to 4 dtex. In this case dtex or decitex should be understood as the weight in grams of the fibers at an optionally theoretical length of 10,000 m.

The further fibers can have a length of 30 to 80 mm. They are preferably used with a length of 32 to 76 mm, particularly preferably with a length of 35 to 74 mm and quite particularly preferably with a length of 38 to 70 mm.

If the airlaid process is used, then the further fibers can have a length of 5 to 20 mm. They are preferably used with a length of 6 to 19 mm, particularly preferably with a length of 7 to 18 mm and quite particularly preferably with a length of 8 to 17 mm.

Furthermore the fibers or the fibrous structures can have additional additives. In this case pharmacologically active substances or drugs, such as antibiotics, analgesics, anti-infectives, anti-inflammatory agents, agents to promote wound healing or the like, antimicrobial, antibacterial or antiviral agents, haemostatic agents, enzymes, amino acids, antioxidants, peptides and/or peptide sequences, polysaccharides (e.g. chitosan), growth factors (e.g. purines, pyrimidines), live cells, β-tricalciumphosphate, hydroxyapatite, particularly specially hydroxyapatite nanoparticles, odour-adsorbing additives such as activated carbon, cyclodextrins, metals such as silver, gold, copper, zinc, carbon compounds, such as activated carbon, graphite or the like and/or processing agents such as surfactants, wetting agents, brighteners, antistatics can be used.

By the use of at least one additive the fibers or fibrous structures can also advantageously be provided with further physical, chemical and biological properties. Thus for example a coating of the fibers or fibrous structures with silver facilitates an antibacterial effect of the fibers or fibrous structures.

The fibers or fibrous structures can have a particularly high absorption capacity for water, aqueous solutions and wound exudate. The fibers or fibrous structures can have an absorption capacity for 0.9% sodium chloride solution from 300 to 3500% by weight. In the case of fibers and/or one-dimensional and two-dimensional fibrous structures the absorption capacity for 0.9% sodium chloride solution is preferably from 300 to 3500% by weight, particularly preferably from 400 to 2500% by weight and quite particularly preferably from 500 to 2000% by weight.

The fibers or fibrous structures can have a shrinkage of 1 to 60%. In the case of two-dimensional fibrous structures the shrinkage is preferably a maximum of 50%, particularly preferably a maximum of 45% and quite particularly preferably a maximum of 35%.

According to a further feature of the invention a method for the production of fibers or fibrous structures, one-dimensional, two-dimensional or three-dimensional, comprising fibers made of a first raw fiber material is proposed, in which the fibers are tempered at a predetermined tempering temperature for a predetermined tempering time. In this case the first raw fiber material has unsubstituted or partially substituted polyvinyl alcohol and/or unsubstituted or partially substituted polyvinyl alcohol copolymers.

Fibers or fibrous structures which have gelling properties, in particular hydrogelling properties, can be produced advantageously by this very simple process. For this only one single process step is necessary for stabilising the fibers or fibrous structure, and is designed to be environmentally friendly in such a way that no solvent, by-products or waste products accrue. Moreover contaminants, such as for example brighteners, spinning aids or solvents, which may be contained in the fiber or fibrous structures can be removed by the tempering.

Tempering should be understood to be a process in which a predetermined temperature is maintained for a predetermined time. If fibers are tempered in this way, then the fibers are first of all brought to the predetermined temperature and then kept at this predetermined temperature for the predetermined time. In this case temperature fluctuations which occur of at least +/-10%, in particular +/-5% and preferably +/-1% can be tolerated.

Fibers made of a first raw fiber material with a weight of 0.9 to 10 dtex can be used. They are preferably used with a weight of 1 to 9 dtex, particularly preferably with a weight of 1.5 to 5 dtex and quite particularly preferably with a weight of 1.9 to 2.5 dtex.

The fibers of a first raw fiber material can have a length of 30 to 80 mm. They are preferably used with a length of 32 to 70 mm, particularly preferably with a length of 35 to 65 mm and quite particularly preferably with a length of 38 to 60 mm.

If the airlaid process is used, then the fibers made of a first raw fiber material can have a length of 5 to 20 mm. They are preferably used with a length of 6 to 19 mm, particularly preferably with a length of 7 to 18 mm and quite particularly preferably with a length of 8 to 17 mm.

The predetermined tempering temperature can be chosen so that it is greater than a glass transition temperature of the first raw fiber material used. If a plurality of fibers made of different raw fiber materials is used, then the predetermined tempering temperature is chosen to be greater than the glass transition temperature of the fibers according to the invention made of polyvinyl alcohol and/or of polyvinyl alcohol copolymers. The predetermined tempering temperature can be chosen so that it is lower than a fusion temperature of the first raw fiber material used. If a plurality of fibers made of different raw fiber materials is used, then the predetermined temperature is chosen so that it is preferably below the fusion temperature of all the raw fiber materials used.

The tempering temperature is preferably within a temperature range from 85 to 220° C., particularly preferably from 100° C. to 200° C. and quite particularly preferably from 110° C. to 180° C.

The predetermined tempering time may be from 10 minutes to 14 hours. The tempering time is preferably from 2 to 10 hours, particularly preferably from 3 to 8 hours and quite particularly preferably from 4 to 7 hours.

By the choice of such tempering temperatures and tempering times the cross-linking of the fibers or fibrous structures according to the invention can be carried out particularly carefully for the fibers or fibrous structure. Moreover a differently configured cross-linking is controllable by variation of the tempering temperatures and tempering times, so that the cross-linked fibers or fibrous structures have different properties if required.

In particular a process can be implemented before or after the tempering in order to obtain one-dimensional, two-dimensional or three-dimensional fibrous structures. The respective fibrous structures can be produced from the fibers by means of a process for example as described above.

Thus advantageously the fibers or fibrous structures can be brought into a desired form and bonded in this form by a corresponding bonding process.

Moreover further fibers made of at least one second raw fiber material can also be added.

It is advantageous to carry out the addition of further fibers after the tempering if the further fibers are affected for example by the tempering process and the tempering of the further fibers leads to unwanted results.

Furthermore an after-treatment can be carried out. Moreover an addition of processing agents is possible, in particular before the bonding process. Likewise an addition of, for example, previously described additives may be performed.

Post-bonding, sterilisation, irradiation, coating, application of brighteners, chemical modification or further processing may be carried out as possible after-treatment.

The individual method steps, tempering, bonding, addition of further fibers, addition of additives, addition of processing agents, and after-treatment can be repeated a number of times in any sequence. The fibers or the fibrous structures should be tempered at least once at a predetermined tempering temperature for a predetermined tempering time.

Brighteners, antistatic agents, surfactants, stabilisers, lubricants or the like may be used as processing agents.

In a preferred variant of the production process, fibers made of a first raw fiber material, in particular polyvinyl alcohol staple fibers, for cross-linking at a predetermined tempering temperature which is above the glass transition temperature of the fibers made of a first raw fiber material, in particular for 4 to 7 hours, are tempered. This may optionally be followed by an addition of further fibers, in particular non-gelling fibers, particularly preferably polyester fibers, with a proportion of 10 to 50% by weight. Then a two-dimensional fibrous structure, such as for example a nonwoven fabric, can be produced from the fibers thus produced, optionally using processing agents, such as for example brighteners or antistatic agents, by means of a bonding process.

In another preferred variant of the production process fibers made of a first raw fiber material can be optionally combined with further fibers made of a second raw fiber material, wherein the proportion of further fibers is preferably 10-50% by weight. However, it is also possible to use only fibers made of a first raw fiber material. Polyvinyl alcohol fibers are preferably used as fibers made of a first raw fiber material and polyester fibers are preferably used as further fibers made of a second raw fiber material. A two-dimensional fibrous structure such as for example a nonwoven fabric can be produced from these fibers by means of a bonding process. Next the two-dimensional fibrous structure thus produced can be tempered at a tempering temperature above the glass transition temperature of the fibers made of a first raw fiber material. A two-dimensional fibrous structure produced in this way may optionally be subjected to after-treatment.

According to a further feature of the invention the use of fibers or fibrous structures as described above is proposed, wherein such fibers or fibrous structures are used for production of materials for medical applications, in particular for wound dressings, bandages, suture materials, implants, tissue engineering scaffolds, medication, or for production of carrier materials, insulating materials, filter materials, or are used in the production of hygiene, cosmetic and household products, technical absorber products such as cable sheathings, products for the foodstuff sector such as foodstuff packaging, or are used in fabric construction. Hygiene products may be understood to be inter alia feminine hygiene products, diapers and incontinence products. Likewise household products encompass cleaning materials.

The aforementioned advantages are produced inter alia for the respective use.

As a further feature of the invention a bandage or a wound dressing is proposed, containing fibers or fibrous structures as described above. Such fibers or fibrous structures can preferably be used in the field of modern wound care, in particular for moist wound treatment.

Such bandages or wound dressings can be used in a similar manner to conventional bandages or wound dressings, such as for example gauze bandages, but have the advantageous hydrogelling properties, so that advantageously improved wound care can be achieved by bandages or wound dressings according to the invention.

SUMMARY OF THE INVENTION

Example 1: Production of Tempered Fibers from Polyvinyl Alcohol

Polyvinyl alcohol fibers (2.2 dtex) are tempered at 150° C., in order to achieve cross-linking of the polyvinyl alcohol (PVA).

After a tempering time of 2 hours stability of the PVA fibers ensues, which is demonstrated by the formation of stable hydrogelling fibers in 0.9% aqueous sodium chloride solution. The stability of the fibers increases with the tempering time. With a tempering time of 4 to 7 hours the fibers exhibit a high stability.

After the tempering the absorption of 0.9% aqueous sodium chloride solution of the fibers is determined. The determination of the absorption takes place in accordance with DIN 53923. Instead of the absorption of water described in DIN 53923, the absorption of 0.9% aqueous sodium chloride solution is determined. Depending on the tempering time and thus the degree of cross-linking, the absorption of 0.9% aqueous sodium chloride solution amounts to between 300 and 3500% by weight.

The tempered PVA fibers can be further processed to produce nonwoven fabrics. Nonwoven fabrics are produced from PVA fibers or from PVA fibers with the addition of other fibers such as for example polyester. Depending on the addition of fibers and the degree of cross-linking, the nonwoven fabrics produced from the tempered PVA fibers exhibit a high absorption of 0.9% aqueous sodium chloride solution between 300 and 3500% by weight.

Example 2: Needle-Bonded Nonwoven Fabric Made of Polyvinyl Alcohol

A needle-bonded PVA nonwoven fabric is produced. The needle-bonded polyvinyl alcohol nonwoven fabric made of PVA fibers (2.2 dtex) is tempered at 150° C. in order to achieve cross-linking of the polyvinyl alcohol.

After a tempering time of 2 hours, stability of the PVA nonwoven fabrics ensues, which is demonstrated by the formation of stable hydrogelling fibers in 0.9% aqueous sodium chloride solution. The stability of the nonwoven fabrics increases with the tempering time. With a tempering time of 4 to 7 hours the nonwoven fabrics exhibit a high stability.

After the tempering the absorption of 0.9% aqueous sodium chloride solution of the nonwoven fabric is determined as in Example 1.

Depending on the tempering time and thus the degree of cross-linking, the absorption of 0.9% aqueous sodium chloride solution amounts to between 300 and 2000% by weight.

Moreover the shrinkage of the bonded nonwoven fabrics in 0.9% aqueous sodium chloride solution is determined. For this purpose 10.0 cm×10.0 cm (area 1) large pieces of nonwoven fabric are stamped out and these are immersed in 0.9% aqueous sodium chloride solution. The nonwoven fabrics are removed from the solution and drained for 2 minutes. Then the size of the nonwoven fabrics is measured [±1 mm] (area 2). The shrinkage of the nonwovens is calculated according to the following formula:

$$\text{shrinkage } [\%] = 100 - \frac{\text{area 2}[\text{cm}^2]}{\text{area 1}[\text{cm}^2]} * 100$$

The shrinkage of the polyvinyl alcohol nonwoven fabrics, depending on the tempering time and thus the degree of cross-linking of the nonwoven fabrics is between 30 and 60%.

Example 3: Calender-Bonded Nonwoven Fabric Made of Polyvinyl Alcohol

A calender-bonded polyvinyl alcohol nonwoven fabric made of PVA fibers (2.2 dtex) is tempered at 150° C. in order to achieve cross-linking of the polyvinyl alcohol.

After a tempering time of 2 hours, stability of the PVA nonwoven fabrics ensues, which is demonstrated by the formation of stable hydrogelling fibers in 0.9% aqueous sodium chloride solution. The stability of the nonwoven fabrics increases with the tempering time. With a tempering time of 4 to 7 hours the fibers exhibit a high stability.

After the tempering the absorption of 0.9% aqueous sodium chloride solution of the nonwoven fabric is determined as in Example 1.

Depending on the tempering time and thus the degree of cross-linking, the absorption of 0.9% aqueous sodium chloride solution amounts to between 300 and 2000% by weight.

Moreover the shrinkage of the nonwoven fabrics in 0.9% aqueous sodium chloride solution is determined as in Example 2. Depending on the tempering time and thus the degree of cross-linking of the nonwoven fabrics, the shrinkage of the polyvinyl alcohol nonwoven fabrics is between 30 and 60%.

Example 4: Polyvinyl Alcohol/Polyester Mixed Nonwoven Fabrics

Needle-bonded mixed nonwoven fabrics are produced from polyvinyl alcohol fibers (2.2 dtex) and polyester fibers (1.7 dtex). The proportion of polyester fibers in the mixed nonwoven fabric is between 10 and 50%. The nonwovens are tempered at 150° C. in order to achieve cross-linking of the polyvinyl alcohol fibers in the nonwoven.

After a tempering time of 2 hours, stability of the nonwoven fabrics ensues, which is demonstrated by the formation of stable, hydrogelling nonwoven fabrics in 0.9% aqueous sodium chloride solution. The stability of the nonwoven fabrics increases with the tempering time. With a tempering time of 4 to 7 hours the nonwoven fabrics exhibit a high stability.

After the tempering the absorption of 0.9% aqueous sodium chloride solution of the nonwoven fabric is determined as in Example 1.

As a function of the proportion of polyester in the nonwoven fabric the absorption of 0.9% aqueous sodium chloride solution is between 500 and 3000% by weight. As the proportion of polyester in the nonwoven fabric rises from 10% to 50%, the absorption increases.

Moreover the shrinkage of the bonded nonwoven fabrics in 0.9% aqueous sodium chloride solution is determined as in Example 2.

As a function of the proportion of polyester in the nonwoven, the shrinkage of the nonwoven fabrics is between 1 and 45%. Thus the shrinkage of the mixed nonwoven fabrics is significantly lower by comparison with polyvinyl alcohol nonwoven fabrics without the addition of polyester fibers. As the proportion of polyester in the nonwoven fabric increases the shrinkage decreases.

Example 5: Polyvinyl Alcohol/Polyester Mixed Nonwoven Fabrics

Needle-bonded mixed nonwoven fabrics are produced from polyvinyl alcohol fibers (2.2 dtex) and polyester fibers (3.3 dtex). The proportion of polyester fibers in the mixed nonwoven fabric is between 10 and 50%. The nonwoven fabrics are tempered at 150° C. in order to achieve cross-linking of the polyvinyl alcohol fibers in the nonwoven.

After a tempering time of 2 hours, stability of the nonwoven fabrics ensues, which is demonstrated by the formation of stable, hydrogelling nonwoven fabrics in 0.9% aqueous sodium chloride solution. The stability of the nonwoven fabrics increases with the tempering time. With a tempering time of 4 to 7 hours the fibers exhibit a high stability. After the tempering the absorption of 0.9% aqueous sodium chloride solution of the nonwoven fabric is determined as in Example 1.

As a function of the proportion of polyester in the nonwoven fabric the absorption of 0.9% aqueous sodium chloride solution is between 500 and 3500% by weight. As the proportion of polyester in the nonwoven fabric rises from 10% to 50%, the absorption increases.

Moreover the shrinkage of the bonded nonwoven fabrics in 0.9% aqueous sodium chloride solution is determined as in Example 2.

As a function of the proportion of polyester in the nonwoven fabric, the shrinkage of the nonwoven fabrics is between 1 and 45%. Thus the shrinkage of the mixed nonwoven fabrics is significantly lower by comparison with polyvinyl alcohol nonwovens without the addition of polyester fibers. As the proportion of polyester in the nonwoven increases the shrinkage decreases.

Example 6: Determination of the Thermodesorption

In the determination of the thermodesorption, by heating a sample of fibers or fibrous structures at 150° C. for 20 minutes, organic components contained in the fibers are released, focussed by means of a cryo trap and then injected into the GC/MS by means of a cold feed system. A GERSTEL thermodesorption system and a KAS GERSTEL cold feed system are used. The released components are detected by means of GC/MS. In this case an Agilent Technologies 6890N Network GC system, and Agilent Technologies 5973 mass-selective detector are used.

In non-tempered PVA fibers, dimethylsulphoxide and fatty alcohol ethoxylates, for example from the brightener, can be detected by means of thermodesorption. After the tempering the tempered PVA fibers are likewise examined by means of thermodesorption. After tempering no dimethylsulphoxide or fatty alcohol ethoxylates are detected. Thus contaminants such as for example spinning aids, solvents or brighteners, contained in the nonwoven fabric or the fibers can be removed by the tempering.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the attached claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B." Further, the recitation of "at least one of A, B, and C" should be interpreted as one or more of a group of elements consisting of A, B, and C, and should not be interpreted as requiring at least one of each of the listed elements A, B, and C, regardless of whether A, B, and C are related as categories or otherwise.

The invention claimed is:

1. A plurality of fibers, comprising:
    at least 30 wt. % of first fibers made of a first raw fiber material consisting of an unsubstituted polyvinyl alcohol, a partially substituted polyvinyl alcohol, or a mixture thereof; and
    optionally, 1 wt % to 70 wt % of second fibers consisting of a polyolefin, polyamide, polyester, polyacrylonitrile, polyvinyl chloride, polyester amide, polyvinyl amine, polyvinyl acetate, polyethylene glycol, polyvinylpyrrolidone, polyurethane, gelatine, collagen, or a mixture of two or more of any of these,
    wherein the polyvinyl alcohol is directly cross-linked by tempering at a temperature of 100 to 200° C., such that cross-linked polyvinyl alcohol is present,
    wherein the first fibers have a fiber titer of 1.5 to 5 dtex,
    wherein the first and second fibers comprise no polyacrylate,
    wherein the plurality has an absorption capacity for 0.9% sodium chloride solution of from 300 to 3500% by weight as measured by DIN 53923, and
    wherein the plurality is configured to be gelling or hydrogelling and has a structural shrinkage of at most 60%.

2. The plurality of claim 1, comprising, as the fibers, at least 90 wt. % of the first fibers.

3. The plurality of claim 1, comprising, as the fibers, at least 95 wt. % of the first fibers.

4. The plurality of claim 1, wherein the absorption capacity for 0.9% sodium chloride solution is at least 500% by weight.

5. The plurality of claim 1, wherein the first fiber is polyvinyl alcohol and the second fiber is polyester.

6. The plurality of claim 1, wherein the polyvinyl alcohol is directly cross-linked by tempering for a period of time from 4 to 7 hours.

7. The plurality of claim 1, further comprising:
    an additive comprising a pharmacologically active substance, a drug, an antibiotic, an analgesic, an anti-infective, an anti-inflammatory, a haemostatic, a wound healing promoting, an antimicrobial, an antibacterial, an antiviral, an enzyme, an amino acid, an antioxidant, a peptide, a peptide sequence, a polysaccharide, a chitosan, a growth factor, a purine, a pyrimidine, a live cell, β-tricalciumphosphate, hydroxyapatite, a odoradsorber, a cyclodextrin, a metal, a carbon compound, a processing agent, or a mixture thereof.

8. The plurality of claim 7, wherein the additive comprises silver, gold, copper, zinc, or graphite.

9. A medical application material, wound dressing, bandage, suture material, implant, tissue engineering scaffold, drug, carrier material, insulating material, filter material, technical absorber product, foodstuff sector product, hygiene product, cosmetic product, or household product, comprising:
    the plurality of claim 1.

10. A method for producing the plurality of claim 1, the method comprising:
    tempering the first fibers at a predetermined tempering temperature in a range of from 100 to 200° C. for a predetermined tempering time.

11. The method of claim 10, wherein the predetermined tempering temperature is
    greater than a glass transition temperature of the first raw fiber material,
    less than a fusion temperature of the first raw fiber material, or
    greater than a glass transition temperature of the first raw fiber material and less than a fusion temperature of the first raw fiber material.

12. The method of claim 10, wherein the predetermined tempering time is from 10 minutes to 14 hours.

13. The method of claim 10, further comprising:
    bonding the fibers to thereby produce a one-dimensional, two-dimensional, or three-dimensional fibrous structure.

14. The method of claim 10, further comprising:
    adding second fibers made of at least one second raw fiber material.

* * * * *